US009096616B2

(12) United States Patent
Trukhan et al.

(10) Patent No.: US 9,096,616 B2
(45) Date of Patent: Aug. 4, 2015

(54) PROCESS FOR PREPARING A POROUS METAL-ORGANIC FRAMEWORK COMPOSED OF ZINC METHYLIMIDAZOLATE

(75) Inventors: Natalia Trukhan, Ludwigshafen (DE); Ulrich Müller, Neustadt (DE)

(73) Assignee: BASF SE, Ludwigshafen (DE)

( * ) Notice: Subject to any disclaimer, the term of this patent is extended or adjusted under 35 U.S.C. 154(b) by 298 days.

(21) Appl. No.: 13/542,971

(22) Filed: Jul. 6, 2012

(65) Prior Publication Data

US 2013/0012717 A1 Jan. 10, 2013

Related U.S. Application Data

(60) Provisional application No. 61/504,716, filed on Jul. 6, 2011.

(51) Int. Cl.
*C07F 3/06* (2006.01)

(52) U.S. Cl.
CPC .......................................... *C07F 3/06* (2013.01)

(58) Field of Classification Search
CPC ........................................................ C07F 3/06
See application file for complete search history.

(56) References Cited

U.S. PATENT DOCUMENTS

| | | | | |
|---|---|---|---|---|
| 3,792,016 | A | 2/1974 | Hill et al. | |
| 8,658,562 | B2 | 2/2014 | Loiseau et al. | |
| 2009/0183996 | A1 * | 7/2009 | Richter et al. | 205/424 |
| 2010/0160661 | A1 | 6/2010 | Schubert et al. | |

FOREIGN PATENT DOCUMENTS

| | | |
|---|---|---|
| EP | 1070538 | 1/2001 |
| EP | 1785428 | 5/2007 |
| WO | WO-01/46290 | 6/2001 |
| WO | WO-2007/087434 | 8/2007 |
| WO | WO-2007/131955 | 11/2007 |
| WO | WO-2010/058123 | 5/2010 |

OTHER PUBLICATIONS

Huang et al. "Ligand-Directed Strategy for Zeolite-Type Metal-Organic Frameworks: Zinc(II) Imidazolates with Unusual Zeolitic Topologies", Angew. Chemie, vol. 118, 2006, pp. 1587-1589.*

Pan et al. "Rapid synthesis of zeolitic imidazolate framework-8 (ZIF-8) nanocrystals in an aqueous system" Chemical Communications, 2011, vol. 47, pp. 2071-2073.*

Cravillon, Janosch et al., "Rapid Room-Temperature Synthesis and Characterization of Nanocrystals of a Prototypical Zeolitic Imidazolate Framework", *Chem. Mater.*, vol. 21 2009 , 14 pgs.

Huang, Xiao-Chun et al., "Ligand-Directed Strategy for Zeolite-Type Metal-Organic Frameworks: Zinc(II) Imidazolates with Unusual Zeolitic Topologies", *Angew. Chemie.*, vol. 118 2006 , pp. 1587-1589.

PCT Written Opinion and Search Report mailed Nov. 15, 2012, 10 pgs.

Park, Kyo S. et al., "Exceptional chemical and thermal stability of zeolitic imidazolate frameworks", *PNAS*, vol. 103, No. 27 Jul. 5, 2006, 10186-10191.

Supplementary European Search Report in EP12807882, dated Apr. 23, 2015, 2 pages.

Bauman, John B., et al., Imidazole Complexes of Nickel(II), Copper(II), Zinc(II), and Silver(1), *Inorganic Chemistry*, vol. 3 No. 3 Mar. 1964, 368-373.

* cited by examiner

*Primary Examiner* — Joseph Kosack
(74) *Attorney, Agent, or Firm* — Servilla Whitney LLC

(57) ABSTRACT

Described is a process for preparing a porous metal-organic framework comprising at least one at least bidentate organic compound coordinated to at least one metal ion, where the at least one metal ion is a zinc ion and the at least one at least bidentate organic compound is based on 2-methylimidazole, which comprises the steps (a) addition of a first water-based solution comprising zinc ions to a second water-based solution comprising 2-methylimidazole, with a suspension being formed after addition of the second solution; (b) addition of a third solution comprising a strong base to the suspension formed in step (a).

17 Claims, No Drawings

PROCESS FOR PREPARING A POROUS METAL-ORGANIC FRAMEWORK COMPOSED OF ZINC METHYLIMIDAZOLATE

CROSS-REFERENCE TO RELATED APPLICATIONS

This application claims priority under 35 U.S.C. §119(e) to U.S. Provisional Application No. 61/504,716, filed Jul. 6, 2011, the disclosure of which is incorporated herein by reference in its entirety.

FIELD

The present invention relates to a process for preparing a porous metal-organic framework composed of zinc methylimidazolate.

BACKGROUND

Porous metal-organic frameworks are known in the prior art and form an interesting class of substances which can be an alternative to zeolites for various applications.

Numerous processes have been developed for preparing such porous metal-organic frameworks. Typically, a metal salt is reacted with the at least bidentate organic compound, for example a dicarboxylic acid, in a suitable solvent under superatmospheric pressure and at elevated temperature.

These preparative processes frequently do not provide a basis for the production of relatively large amounts.

Preparative processes of this type are also known for the zinc 2-methylimidazolate known in the prior art as metal-organic framework.

WO 2007/131955 A1 describes, for example, the electrochemical preparation of this framework. Here, zinc is made available to the reaction space by anodic oxidation. Despite the very good yields, this process is expensive and has only limited suitability for industrial production.

J. Cravillon et al., Chem. Mater. 21 (2009), 1410-1412, describe the preparation of the framework in only moderate yields in methanol and N,N-dimethylformamide (supporting information).

X.-C. Huang et al., Angew. Chem. 118 (2006), 1587-1589, describe the preparation of the framework, which is concluded only after one month and gives moderate yields.

Despite the preparative processes known in the prior art, there is a need for new processes in which the disadvantages of the prior art are at least partly overcome and, in particular, allow preparation of the framework in relatively large amounts, in particular in very good absolute yields (based on a starting material) and yields on a time basis (space-time yield).

SUMMARY

One aspect of the present invention pertains to a process for preparing a porous metal-organic framework comprising at least one at least bidentate organic compound coordinated to at least one metal ion. The at least one metal ion may a zinc ion and the at least one at least bidentate organic compound may be based on 2-methylimidazole. In one or more embodiments of this aspect, the process comprises (a) adding a first water-based solution comprising zinc ions to a second water-based solution comprising 2-methylimidazole to provide a suspension, and then (b) adding a third solution comprising a strong base to the suspension formed in step (a).

According to one or more embodiments, the molar ratio of zinc ions added to 2-methylimidazole added after the end of the addition in step (a) is in the range from about 1:5 to about 1:1. In some embodiments, the molar proportion of zinc based on the total amount of the suspension before step (b) is in the range from about 0.2 to about 0.7 mmol of zinc/g of suspension. In some embodiments, the molar proportion of zinc based on the total amount of the suspension after step (b) may in the range from about 0.1 to about 0.5 mmol of zinc/g of suspension.

The first water-based solution may be a zinc sulfate solution. In some embodiments, the first, the second or the first and the second water-based solution is a methanol/water solution. In some embodiments in which one or more solutions contain methanol, the molar ratio of zinc to methanol after the end of the addition in step (b) is in the range from about 1:5 to about 1:50.

The third solution may be a water-based alkali metal hydroxide solution. In some embodiments, the molar ratio of zinc to alkali metal hydroxide after the end of the addition in step (b) is in the range from about 1:5 to about 1:1.

According to one or more embodiments, the pH before step (b) may be below about 6.5. In one or more embodiments, the pH after step (b) may be greater than about 6.0.

In some embodiments, the solids yield of metal-organic framework may be in the range from about 2 to about 15% by weight.

In one or more embodiments, at least one of the steps (a) and (b) may be carried out at a temperature in the range from about 10° C. to about 30° C. One or more embodiments provide that at least one of the steps (a) and (b) may be carried out at an absolute pressure of not more than about 2 bar. In some embodiments, at least one of the steps (a) and (b) is carried out with mixing of the suspension.

In one or more embodiments, the process further comprises (c) isolation of the metal-organic framework after step (b). In some embodiments, isolation in step (c) is carried out by filtration with optional subsequent washing and/or drying.

Another aspect of the present invention pertains to a metal-organic framework made by any of the embodiments of the processes described herein.

DETAILED DESCRIPTION

One or more embodiments of the present invention provide a process that overcomes one or more disadvantages of the prior art.

One or more embodiments may achieve a process for preparing a porous metal-organic framework comprising at least one at least bidentate organic compound coordinated to at least one metal ion, where the at least one metal ion is a zinc ion and the at least one at least bidentate organic compound is based on 2-methylimidazole, which comprises the steps (a) addition of a first water-based solution comprising zinc ions to a second water-based solution comprising 2-methylimidazole, with a suspension being formed after addition of the second solution;

(b) addition of a third solution comprising a strong base to the suspension formed in step (a).

It has surprisingly been found that high space-time yields can be achieved when the abovementioned features of the process of the invention are adhered to. In particular, it is surprising that the framework obtained can be obtained not only virtually quantitatively but also with very good specific surface areas.

The porous metal-organic framework prepared by the process of one or more embodiments of the invention comprises at least one metal ion which is a zinc ion. However, it is likewise possible for more than one metal ion to be present in the porous metal-organic framework.

These one or more metal ions other than zinc can be located in the pores of the metal-organic framework or participate in formation of the lattice of the framework. In the latter case, such a metal ion would likewise bind the at least one at least bidentate organic compound or a further at least bidentate organic compound.

Possible metal ions used in one or more embodiments are in principle all metal ions which are suitable as part of the porous metal-organic framework. If the porous metal-organic framework comprises more than one metal ion, these metal ions can be present in a stoichiometric or nonstoichiometric amount. If coordination sites are occupied by a further metal ion and this is present in a nonstoichiometric ratio to the abovementioned metal ion, such a porous metal-organic framework can be considered to be a doped framework. The preparation of such doped metal-organic frameworks in general is described in EP-A 1 785 428.

In some embodiments, the porous metal-organic framework may have only one metal ion (zinc ion).

In addition, the porous metal-organic framework may, after the reaction according to one or more embodiments of the invention, be impregnated with a further metal in the form of a metal salt. An impregnation process is described, for example, in EP-A 1070538.

If a further metal ion is present in a stoichiometric ratio to zinc, mixed metal frameworks are obtained. Here, the further metal ion can participate in the construction of the framework or not participate.

In some embodiments, the framework may be made up of only zinc ions and the at least one at least bidentate organic compound.

In addition, the porous metal-organic framework may comprise at least one at least bidentate organic compound based on 2-methylimidazole.

For the purposes of one or more embodiments of the present invention, the term "based" refers to 2-methylimidazole or its anion.

The metal-organic framework may also have one or more further at least bidentate organic compounds which are different from 2-methylimidazole.

For example, the framework of one or more embodiments may comprise nitrogen-based organic compounds as are described in WO 2007/131955 A1.

Accordingly, the at least one further organic compound may be a monocyclic, bicyclic or polycyclic ring system which is derived from at least one heterocycle selected from the group consisting of pyrrole, alpha-pyridone and gamma-pyridone and has at least two ring nitrogens, where the ring system is unsubstituted or has one or more substituents selected independently from the group consisting of halogen, $C_{1-6}$-alkyl, phenyl, $NH_2$, $NH(C_{1-6}\text{-alkyl})$, $N(C_{1-6}\text{-alkyl})_2$, OH, Ophenyl and $OC_{1-6}$-alkyl, where the substituents $C_{1-6}$-alkyl and phenyl are unsubstituted or have one or more substituents selected independently from the group consisting of halogen, $NH_2$, $NH(C_{1-6}\text{-alkyl})$, $N(C_{1-6}\text{-alkyl})_2$, OH, Ophenyl and $OC_{1-6}$-alkyl, with the exception of 2-methylimidazole.

In accordance with various embodiments of the present invention, the term "$C_{1-6}$-alkyl" refers to an alkyl group having from 1 to 6 carbon atoms. Non-limiting examples are methyl, ethyl, n-propyl, i-propyl, n-butyl, i-butyl, sec-butyl, t-butyl, pentyl, hexyl. In some embodiments, the radical is selected from methyl and ethyl. If a substituted $C_{1-6}$-alkyl radical is present, at least one hydrogen atom is replaced by another substituent.

Furthermore, in accordance with various embodiments of the present invention, the term "halogen" refers to fluorine, chlorine, bromine or iodine. In one or more embodiments, the halogen is fluorine or chlorine.

As indicated above, the further organic compound can be a monocyclic, bicyclic or polycyclic ring system which is derived at least from one of the heterocycles selected from the group consisting of pyrrole, alpha-pyridone and gamma-pyridone. All these three heterocycles have a ring nitrogen bearing a hydrogen which can be eliminated in at least one mesomeric structure. It is thus possible for the pyrrole, alpha-pyridone or gamma-pyridone to be deprotonated. This forms a negative charge which can at least partially compensate the positive charge of the at least one metal ion.

In accordance with one or more embodiments, the term "derive" means that the monocyclic, bicyclic or polycyclic ring system has at least one substructure which corresponds to pyrrole, alpha-pyridone or gamma-pyridone. In addition, two or all three heterocycles can also be present as substructure in the ring system.

In accordance with one or more embodiments, the term "derive" also means that the three abovementioned heterocycles do not have to be present in neutral form but can optionally also occur as anion or cation, so that the oxidation can also be carried out in the presence of these ions.

In addition, it has to be taken into account that at least one of the heterocycles representing a substructure of the ring system is deprotonated during the reaction.

Furthermore, the term "derive" means, according to one or more embodiments of the present invention, that the substructure of at least one of the three heterocycles can have substituents and one or more ring carbons can be replaced by a heteroatom.

Of course, the ring system can also be one of the heterocycles pyrrole, alpha-pyridone or gamma-pyridone itself or the ring system can likewise be made up of substructures which are selected exclusively from the group consisting of pyrrole, alpha-pyridone and gamma-pyridone. In this case, too, the above-described modifications are possible.

Finally, according to one or more embodiments, at least one hydrogen which in at least one mesomeric structure is not the hydrogen bound to said nitrogen is replaced by a bond by means of which the corresponding heterocycle is bound to the remainder of the ring system.

If the ring system is a monocyclic ring system, this may be derived from pyrrole or alpha-pyridone or gamma-pyridone.

However, the ring system can also be a bicyclic ring system. This is the case when, for example, two rings which are joined to one another via a single covalent bond or via a group R are present in the ring system. Here, one ring has to be derived from pyrrole, alpha-pyridone or gamma-pyridone.

In one or more embodiments, R can be —O—, —NH—, —S—, —N═N— or an aliphatic branched or unbranched saturated or unsaturated hydrocarbon having from 1 to 4 carbon atoms which may be interrupted by one or more independent atoms or functional groups selected from the group consisting of —O—, —NH—, —S— and —N═N—.

Furthermore, the bicyclic ring system can be a fused ring system.

Non-limiting examples are benzofused derivatives derived from pyrrole, alpha-pyridone and gamma-pyridone.

In addition, the bicyclic ring system may be a bridged ring system.

In several embodiments, the ring system can likewise be a polycyclic ring system having 3, 4 or more rings. Here, the rings can be joined via a single covalent bond and/or a group R and/or be present in fused form and/or as bridged ring system.

The ring system has at least two ring nitrogens. At least one of the two ring nitrogens is the nitrogen present in the ring which is derived from pyrrole, alpha-pyridone and gamma-pyridone. In addition, at least one further ring nitrogen has to be present. If the ring system is a system having more than one ring, the at least second ring nitrogen can be present in the ring derived from pyrrole, alpha-pyridone or gamma-pyridone or, if the at least one further ring is not derived from these three heterocycles, in this ring. In specific embodiments, there are at least two ring nitrogens present in one ring of the ring system.

In one or more embodiments, the ring is derived from pyrazole, imidazole (with the exception of 2-methylimidazole), pyridazin-2-one and pyrimidin-2-one or pyrimidin-4-one.

In several embodiments, in addition to the two ring nitrogens, further ring nitrogens can be present. For example, the ring system can have 3, 4, 5 or more ring nitrogens.

In accordance with several embodiments, if more than two ring nitrogens are present, all ring nitrogens can be present in one ring of the ring system or be distributed over more than one ring up to all rings of the ring system.

When, for example, three ring nitrogens are present, these may be present in the ring which is derived from pyrrole, alpha-pyridone or gamma-pyridone. The resulting substructure of the ring may then be derived from a triazole such as 1,2,3-triazole or 1,2,4-triazole.

In one or more other embodiments, the ring system can have further heteroatoms in the ring. These can be, for example, oxygen or sulfur. However, in some embodiments, the ring system does not include any heteroatoms besides nitrogen.

In several embodiments, if the ring system has more than one ring, this ring can be saturated or unsaturated. The at least one further ring may have an at least partially conjugated double bond system or may be aromatic in nature.

The ring system may be unsubstituted.

Furthermore, the ring system can have one or more substituents. If a plurality of substituents are present, these can be identical or different.

The substituents bound to the ring system can be halogen, $C_{1-6}$-alkyl, phenyl, $NH_2$, $NH(C_{1-6}\text{-alkyl})$, $N(C_{1-6}\text{-alkyl})_2$, OH, Ophenyl or $OC_{1-6}$-alkyl.

In one or more embodiments, if at least one of the above-mentioned substituents on the ring system is a $C_{1-6}$-alkyl or phenyl, these can likewise be unsubstituted or have one or more substituents. Here too, when a plurality of substituents are present, it is possible for these to be identical or different. These are selected from the group consisting of halogen, $NH_2$, $NH(C_{1-6}\text{-alkyl})$, $N(C_{1-6}\text{-alkyl})$, $N(C_{1-6}\text{-alkyl})_2$, OH, Ophenyl and $OC_{1-6}$-alkyl.

If the $C_{1-6}$-alkyl group occurs more than once, these alkyl groups can be identical or different.

In accordance with one or more embodiments of the present invention, the hydroxy or keto group of the alpha-pyridone or gamma-pyridone may not be considered to be a substituent since this group is necessary in the ring in order to obtain a ring nitrogen to which hydrogen is bound for at least one mesomeric structure.

In some embodiments, he substituents which are bound to the ring system may not have any further substituents.

Substituents which are bound to the ring system may be $C_{1-6}$-alkyl, phenyl, $NH_2$ and OH. According to one or more embodiments, the ring system includes a $C_{1-6}$-alkyl of $NH_2$ substituent.

In one or more embodiments, the ring system may be selected from the group consisting of

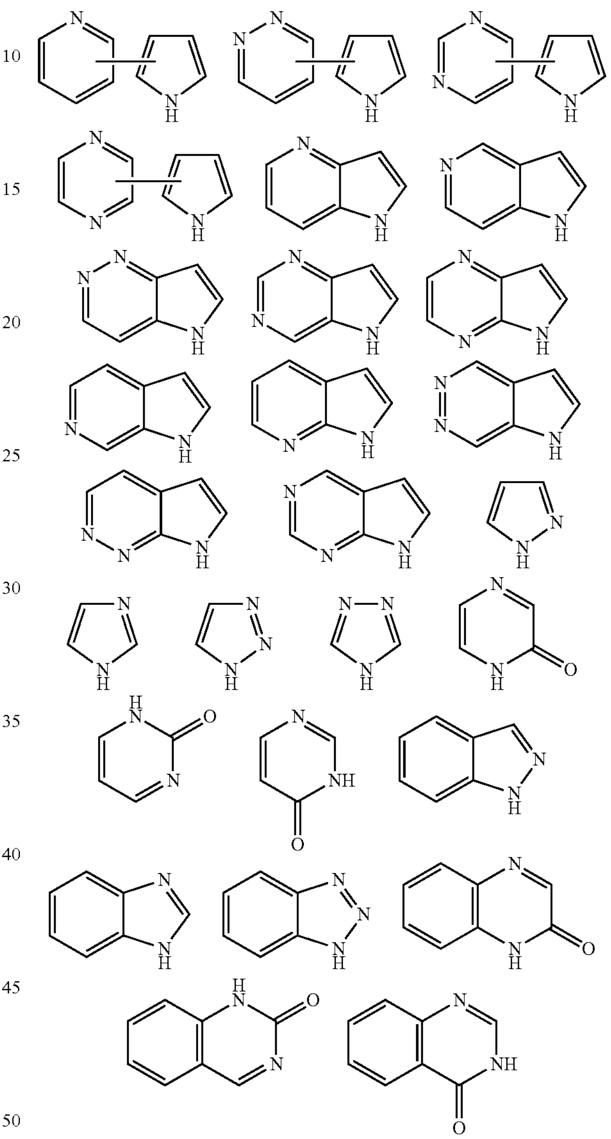

In some embodiments, the ring system may be an imidazole (with the exception of 2-methylimidazole), benzimidazole, triazole, 2-hydroxypyrimidine or 4-hydroxypyrimidine.

The at least one organic compound may be selected from the group consisting of 2-ethylimidazole, benzimidazole, 1,2,4-triazole, 3-amino-1,2,4-triazole, 3,5-diamino-1,2,4-triazole, 2-hydroxypyrimidine and 4-hydroxypyrimidine and protonated forms thereof.

However, in some embodiments the porous metal-organic framework may have only one at least bidentate organic compound (2-methylimidazol(at)e).

One or more embodiments may have a porous metal-organic framework made up of Zn(II) ions to which 2-methylimidazolate is coordinated to form a framework structure.

In step (a) of the process of the invention, a first water-based solution comprising zinc ions is added to a second water-based solution comprising 2-methylimidazole, with a suspension being formed after addition of the second solution.

The first solution is a water-based solution comprising zinc ions. Accordingly, the first solution has a solvent or solvent mixture in which at least zinc ions are present in solution. For the purposes of one or more embodiments, "water-based" means that the solvent is water or a mixture comprising at least 40% by weight (such as at least 50% by weight or even more than 50% by weight) of water, based on the total amount of solvent, is present. In one or more embodiments, the first solution is an aqueous solution having about 100% water as solvent.

The first solution may comprise zinc ions which are typically present in the form of a dissolved zinc compound. It is also possible to use a plurality of zinc compounds. In addition, the first solution can comprise further materials such as further metal compounds. The first solution may comprise only zinc compounds, or only one zinc compound.

The at least one zinc compound is may be an inorganic salt, in particular a halide, sulfide, the salt of an inorganic oxygen-comprising acid, optionally in the form of a hydrate or a mixture thereof.

According to one or more embodiments, the halide is chloride, bromide or iodide.

An inorganic oxygen-comprising acid may be, for example, sulfuric acid, sulfurous acid, phosphoric acid or nitric acid.

One or more embodiments may include zinc sulfate, such as in the form of its heptahydrate.

The zinc compound can also be an organic zinc salt, in particular an acetate, acetylacetonate, citrate or oxalate.

The second solution may be a water-based solution comprising 2-methylimidazole. Accordingly, the second solution has a solvent or solvent mixture in which at least 2-methylimidazole is present in solution. For the purposes one or more embodiments, "water-based" means that the solvent is water or a mixture comprising not more than 70% by weight in several embodiments not more than 60% by weight, not more than 50% by weight, not more than 40% by weight, or less than 40% by weight of water, based on the total amount of solvent, is present.

The second solution may comprise 2-methylimidazole. In addition, the second solution can comprise further materials such as one or more further at least bidentate organic compounds. The second solution may comprise only 2-methylimidazole.

In some embodiments, he molar ratio of zinc ions added to 2-methylimidazole added after the end of the addition in step (a) may be in the range from 1:5 to 1:1, 1:4 to 1:1.1, from 1:3 to 1:1.5, from 1:2.5 to 1:1.75, or from 1:2.

In several embodiments the first, the second or the first and the second water-based solution may be a methanol/water solution. Accordingly, the solvent mixture may be a methanol/water mixture. However, it is also possible to use other mixtures with water. In several embodiments, liquids which have unlimited miscibility with water, e.g. alcohols other than methanol may be used. The proportion by weight of alcohol and in particular methanol in the first solution may not more than 60% by weight, based on the total amount of the mixture, not more than 50% by weight, or less than 50% by weight. In the second solution, the proportion can be at least 30% by weight, at least 40% by weight, at least 50% by weight, at least 60% by weight, or at least 70% by weight.

Addition of the second solution forms a suspension. It will be clear to a person skilled in the art that the commencement of suspension formation is dependent on various factors and thus occurs right at the beginning of addition, between the additions, if the addition is carried out discontinuously, or after the addition is finally complete. Continuous addition may be performed. The suspension comprises framework formed.

In one or more embodiments, in step (b) of the process of the invention, a third solution which is alkaline may be added to the suspension formed in step (a).

Step (b) thus commences when a suspension has been formed in step (a). Steps (a) and (b) can thus occur partially synchronously, i.e. before all of the first and second solution have been added, but after at least some suspension has been formed. Or step (b) may commence only when step (a) is concluded.

The third solution may be alkaline. This can be achieved by using a strong base in a solvent or solvent mixture. It is also possible to use a plurality of bases.

In accordance with one or more embodiments of the invention, the term "strong base" may refer to a Brønsted base which gives a corresponding aqueous solution having a pH given by the equation $pH=14+1\ gc_{Base}$.

As base, one or more embodiments may involve using an alkali metal hydroxide or a mixture of a plurality of different alkali metal hydroxides. Non-limiting examples are, in particular, sodium hydroxide and potassium hydroxide. However, further inorganic hydroxides or carbonates or organic bases such as amines are conceivable. The solvent may be water or, if a mixture is used, a water-based mixture (water-based solution). The proportion of water in this mixture is may be more than 50% by weight. The third solution may be an aqueous solution (100% water as solvent). In particular, a water-based (in particular aqueous) alkali metal hydroxide (in particular NaOH) solution.

In accordance with various embodiments, the addition in steps (a) and (b) can be carried out by known methods. Mention may here be made of, for example, dropwise addition, pouring-in or pumping.

In various embodiments, the molar proportion of zinc based on the total amount of the suspension before step (b) may be in the range from about 0.2 to about 0.7 mmol of zinc/g of suspension; or may be in the range from about 0.35 to about 0.55 mmol of zinc/g of suspension.

The molar proportion of zinc based on the total amount of the suspension after step (b) may be in the range from about 0.1 to about 0.5 mmol of zinc/g of suspension; or may be in the range from about 0.2 to about 0.4 (or may be in the range from about 0.2 to less than about 0.4) mmol of zinc/g of suspension.

The molar ratio of zinc to alkali metal hydroxide after the end of the addition in step (b) may be in the range from about 1:5 to about 1:1, from about 1:4 to about 1:1.1, from about 1:3 to about 1:1.5, from about 1:2.5 to about1:1.75, or about 1:2.

In one or more embodiments, the molar ratio of zinc to methanol after the end of the addition in step (b) may be in the range from about 1:5 to about 1:50, 1:10 to about 1:40, or 1:15 to about 1:30.

The pH before step (b) is may be below about 6.5.

The pH after step (b) may be greater than about 6.0.

In one or more embodiments, at least one of the steps (a) and (b) being carried out at a temperature in the range from about 10° C. to about 30° C.; in the range from about 15° C. to about 25° C., in particular at from about 18° C. to about 23° C. or at room temperature. The steps (a) and (b) may be carried out at the same temperature.

In one or more embodiments, at least one of the steps (a) and (b) may be carried out at an absolute pressure of not more than about 2 bar. However, the pressure is may be not more than 1230 mbar (absolute). The reaction may take place at atmospheric pressure. However, slightly superatmospheric or subatmospheric pressures can occur due to the apparatus. For this reason, the term “atmospheric pressure” refers, for the purposes of the present invention, to the pressure range given by the actual atmospheric pressure ±150 mbar. The steps (a) and (b) may be carried out at the same pressure.

In one or more embodiments, at least one of the steps (a) and (b) may be carried out with mixing of the suspension, in particular both steps. Mixing can be effected by conventional methods. For example, stirring, shaking, circulation or pumped circulation are conceivable here.

Step (b) may be followed by isolation of the metal-organic framework (step c). This can be affected by conventional techniques such as filtration, centrifugation or the like. The isolation in step (c) may be carried out by filtration with optional subsequent washing.

The porous metal-organic framework obtained can be subjected to drying. Spray drying is also possible.

Accordingly, process step (c) may be followed by a drying step which may be carried out after spray drying, should the latter be carried out. The temperature set in drying (with or without spray drying) may be greater than about 60° C., from about 80° C. to about 200° C., or from about 100° C. to about 150° C.

The solids yield of product (framework) may be in the range from about 2 to about 15% by weight, about 4 to about 10% by weight, or from about 5 to about 8% by weight. Here, the solids yield is the ratio of the amount of dry framework to the total amount after the end of step (b) (weight of framework/sum of the weight of the 1st to 3rd solutions).

EXAMPLES

Example 1

Synthesis of Zn-2-methylimidazolate ZIF in MeOH/$H_2O$ Solution at RT

Synthesis Conditions:
MeOH/$H_2O$; RT; 1 bar (atmospheric pressure);
Zn:2-mIm:NaOH:MeOH:$H_2O$=1:2:2:25:111
Experimental Method:

| Starting material | Molar | Calculated | Experimental |
|---|---|---|---|
| 1) 2-methylimidazole (2-mIm) | 0.2 mol | 16.4 g | 16.4 g |
| 2) zinc sulfate*7 water | 0.1 mol | 28.8 g | 28.8 g |
| 3) sodium hydroxide (NaOH) | 0.2 mol | 8.0 g | 8.0 g |
| 4) methanol (MeOH) | 2.5 mol | 80.0 g | 80.0 g |
| 5) water ($H_2O$) | 11.1 mol | 200.0 g | 200.0 g |

Preparation of Solution 1:

In a glass beaker, zinc sulfate is dissolved in 50 g of water and 40 g of methanol (pH=5.2).

Preparation of Solution 2:

In a second glass beaker, 2-methylimidazole is dissolved in 50 g of water and admixed with 40 g of methanol (pH=11.2).

Preparation of Solution 3:

In a third glass beaker, sodium hydroxide is dissolved in 100 g of water (pH=12.8).

The first solution is added dropwise to the second solution over a period of 60 minutes. As time goes on, a white suspension is formed and the pH drops to 6.38. The sodium hydroxide solution is added dropwise to the white suspension over a period of one hour (final pH=7.12). The solid is then filtered off and washed twice with 100 ml of water. The filtercake is dried overnight at 150° C. in a vacuum drying oven.

Weight of product, moist: 56.90 g
Weight of product after drying: 22.46 g
Solids yield of product: 6.74% by weight
Yield based on Zn: 96.9 mol %
Space-time yield (STY): 766 kg/$m^3$/day
Analyses:
Langmuir surface area of product: 1725 $m^2$/g (BET analysis: 1284 $m^2$/g)
Chemical analysis: Zn 28.2% by weight, N 24% by weight, S 0.62% by weight.

Example 2

Synthesis of Zn-2-methylimidazolate ZIF in MeOH/$H_2O$ Solution at RT

Synthesis Conditions:
MeOH/$H_2O$; RT; 1 bar (atmospheric pressure);
Zn:2-mIm:NaOH:MeOH:$H_2O$=1:2:2:25:111
Experimental Method:

| Starting material | Molar | Calculated | Experimental |
|---|---|---|---|
| 1) 2-methylimidazole (2-mIm) | 0.2 mol | 16.4 g | 16.4 g |
| 2) zinc sulfate*7 water | 0.1 mol | 28.8 g | 28.8 g |
| 3) sodium hydroxide (NaOH) | 0.2 mol | 8.0 g | 8.0 g |
| 4) methanol (MeOH) | 2.5 mol | 80.0 g | 80.0 g |
| 5) water ($H_2O$) | 11.1 mol | 200.0 g | 200.0 g |

Preparation of Solution 1:

In a glass beaker, zinc sulfate is dissolved in 50 g of water (pH=5.1).

Preparation of Solution 2:

In a second glass beaker, 2-methylimidazole is dissolved in 50 g of water and admixed with 80 g of methanol (pH=9.5).

Preparation of Solution 3:

In a third glass beaker, sodium hydroxide is dissolved in 100 g of water (pH=12.8).

The first solution is added dropwise to the second solution over a period of 60 minutes. As time goes on, a white suspension is formed and the pH drops to 6.1. The sodium hydroxide solution is added dropwise to the white suspension over a period of one hour (final pH=11.2). The solid is then filtered off and washed 10 times with 100 ml of water. The filtercake is dried at 150° C. in a vacuum drying oven for 48 hours.

Weight of product, moist: 58.57 g
Weight of product after drying: 22.20 g
Solids yield of product: 6.66% by weight
Yield based on Zn: 96.7 mol %
Space-time yield (STY): 758 kg/$m^3$/day
Analyses:
Langmuir surface area of product: 2091 $m^2$/g (BET analysis: 1533 $m^2$/g)
Chemical analysis: Zn 28.3% by weight, N 24.4% by weight, S 0.18% by weight

Example 3

Synthesis of Zn-2-methylimidazolate ZIF in MeOH/$H_2O$ Solution at RT

Synthesis Conditions:
MeOH/$H_2O$; RT; 1 bar (atmospheric pressure);
Zn:2-mIm:NaOH:MeOH:$H_2O$=1:2:2:18.7:111

Experimental Method:

| Starting material | Molar | Calculated | Experimental |
|---|---|---|---|
| 1) 2-methylimidazole (2-mIm) | 0.2 mol | 16.4 g | 16.4 g |
| 2) zinc sulfate*7 water | 0.1 mol | 28.8 g | 28.8 g |
| 3) sodium hydroxide (NaOH) | 0.2 mol | 8.0 g | 8.0 g |
| 4) methanol (MeOH) | 1.87 mol | 60.0 g | 60.0 g |
| 5) water ($H_2O$) | 11.1 mol | 200.0 g | 200.0 g |

Preparation of Solution 1:

In a glass beaker, zinc sulfate is dissolved in 50 g of water (pH=5.1).

Preparation of Solution 2:

In a second glass beaker, 2-methylimidazole is dissolved in 50 g of water and admixed with 60 g of methanol (pH=9.5).

Preparation of Solution 3:

In a third glass beaker, sodium hydroxide is dissolved in 100 g of water (pH=12.8).

The first solution is added dropwise to the second solution over a period of 60 minutes. As time goes on, a white suspension is formed and the pH drops to 6.2. The sodium hydroxide solution is added dropwise to the white suspension over a period of one hour (final pH=11.7).

The solid is then filtered off and washed 10 times with 100 ml of water. The filtercake is dried at 150° C. in a vacuum drying oven for 48 hours.

Weight of product, moist: 46.76 g

Weight of product after drying: 21.89 g

Solids yield of product: 6.99% by weight

Yield based on Zn: 97 mol %

Space-time yield (STY): 804 $kg/m^3$/day

Analyses:

Langmuir surface area of product: 1715 $m^2/g$ (BET analysis: 1258 $m^2/g$)

Chemical analysis: Zn 28.8% by weight, N 23.7% by weight, S 0.54% by weight

The invention claimed is:

1. A process for preparing a porous metal-organic framework, the process comprising (a) adding a first water-based solution comprising zinc ions to a second water-based solution comprising 2-methylimidazole, and, optionally, a further at least bidendate organic compound, to provide a suspension;

(b) adding a third solution comprising a strong base to the suspension formed in step (a) to form a porous metal-organic framework comprising an at least bidendate organic compound based on 2-methylimidazole coordinated and, optionally, a further at least bidendate organic compound coordinated to a zinc ion, wherein the further at least bidendate organic compound is selected from the group consisting of a monocyclic, bicyclic, or polycyclic ring system which is derived from at least one heterocycle selected from the group consisting of pyrrole, alpha-pyridone and gamma-pyridone and has at least two ring nitrogens, where the ring system is unsubstituted or has one or more substituents selected independently from the group consisting of halogen, $C_{1-6}$-,alkyl, phenyl, $NH_2$, NH($C_{1-6}$-alkyl), N($C_{1-6}$-alkyl)$_2$, OH, Ophenyl and $OC_{1-6}$-alkyl, where the substituents $C_{1-6}$-alkyl and phenyl are unsubstituted or have one or more substituents selected independently from the group consisting of halogen, $NH_2$, NH($C_{1-6}$-alkyl), N($C_{1-6}$-alkyl)$_2$, OH, Ophenyl, and $OC_{1-6}$-alkyl.

2. The process according to claim 1, wherein the molar ratio of zinc ions added to 2-methylimidazole added after the end of the addition in step (a) is in the range from about 1:5 to about 1:1.

3. The process according to claim 1, wherein the first water-based solution is a zinc sulfate solution.

4. The process according to claim 1, wherein the first, the second or the first and the second water-based solution is a methanol/water solution.

5. The process according to claim 1, wherein the molar proportion of zinc based on the total amount of the suspension before step (b) is in the range from about 0.2 to about 0.7 mmol of zinc/g of suspension.

6. The process according to claim 1, wherein the molar proportion of zinc based on the total amount of the suspension after step (b) is in the range from about 0.1 to about 0.5 mmol of zinc/g of suspension.

7. The process according to claim 4, wherein the molar ratio of zinc to methanol after the end of the addition in step (b) is in the range from about 1:5 to about 1:50.

8. The process according to claim 1, wherein the third solution is a water-based alkali metal hydroxide solution.

9. The process according to claim 8, wherein the molar ratio of zinc to alkali metal hydroxide after the end of the addition in step (b) is in the range from about 1:5 to about 1:1.

10. The process according to claim 1, wherein the pH before step (b) is below about 6.5.

11. The process according to claim 1, wherein the pH after step (b) is greater than about 6.0.

12. The process according to claim 1, wherein the solids yield of metal-organic framework is in the range from about 2 to about 15% by weight.

13. The process according to claim 1, wherein at least one of the steps (a) and (b) is carried out at a temperature in the range from about 10° C. to about 30° C.

14. The process according to claim 1, wherein at least one of the steps (a) and (b) is carried out at an absolute pressure of not more than about 2 bar.

15. The process according to claim 1, wherein at least one of the steps (a) and (b) is carried out with mixing of the suspension.

16. The process according to claim 1, wherein step (b) is followed by a step (c) isolation of the metal-organic framework.

17. The process according to claim 1, wherein the isolation in step (c) is carried out by filtration with optional subsequent washing and/or drying.

* * * * *